(12) United States Patent
Todd

(10) Patent No.: US 9,409,053 B1
(45) Date of Patent: Aug. 9, 2016

(54) EXERCISE DATA COLLECTION SYSTEM

(71) Applicant: BML PRODUCTIONS, INC., Secaucus, NJ (US)

(72) Inventor: Eric Todd, Old Tappan, NJ (US)

(73) Assignee: BML PRODUCTIONS, INC., Secaucus, NJ (US)

( * ) Notice: Subject to any disclaimer, the term of this patent is extended or adjusted under 35 U.S.C. 154(b) by 0 days.

(21) Appl. No.: 14/797,550

(22) Filed: Jul. 13, 2015

(51) Int. Cl.
*A63B 24/00* (2006.01)

(52) U.S. Cl.
CPC ............. *A63B 24/0062* (2013.01); *A63B 24/00* (2013.01)

(58) Field of Classification Search
CPC ........... A63B 21/0442; A63B 21/1407; A63B 21/015; A63B 21/00; A63B 71/0622; A63B 24/00; A63B 24/0062
See application file for complete search history.

(56) References Cited

U.S. PATENT DOCUMENTS

| | | | |
|---|---|---|---|
| 4,278,095 | A | 7/1981 | Lapeyre |
| 5,598,849 | A | 2/1997 | Browne |
| 6,251,048 | B1 | 6/2001 | Kaufman |
| 6,301,964 | B1 | 10/2001 | Fyfe et al. |
| 7,152,286 | B2 | 12/2006 | Rooney et al. |
| 7,254,516 | B2 | 8/2007 | Case, Jr. et al. |
| 7,651,442 | B2 | 1/2010 | Carlson |
| 8,287,434 | B2 * | 10/2012 | Zavadsky ............... A63B 21/00 482/1 |
| 8,749,380 | B2 | 6/2014 | Vock et al. |
| 8,862,215 | B2 | 10/2014 | Puolakanaho et al. |
| 2003/0069108 | A1 | 4/2003 | Kaiserman et al. |
| 2008/0015089 | A1 * | 1/2008 | Hurwitz ............... A63B 21/015 482/8 |
| 2010/0279822 | A1 * | 11/2010 | Ford ................... A63B 71/0622 482/8 |
| 2011/0165998 | A1 | 7/2011 | Lau et al. |
| 2012/0184871 | A1 | 7/2012 | Jang et al. |
| 2012/0220428 | A1 * | 8/2012 | Carlson .............. A63B 21/1407 482/8 |
| 2013/0005534 | A1 | 1/2013 | Rosenbaum |
| 2014/0207264 | A1 | 7/2014 | Quy |
| 2014/0235409 | A1 | 8/2014 | Salmon et al. |
| 2014/0275821 | A1 | 9/2014 | Beckman |
| 2014/0323271 | A1 * | 10/2014 | Hinds ................. A63B 21/0442 482/8 |

FOREIGN PATENT DOCUMENTS

EP 0336030 A1 11/1989

OTHER PUBLICATIONS

Dartfish Express, downloaded from http://www.dartfish.com/Express (downloaded on Jun. 17, 2015).
"Nike+ FuelBand SE. Activity Tracker & Fitness Monitor," downloaded from http://www.nike.com/us/en_us/c/nikeplus-fuelband (downloaded on Jun. 24, 2015).
"View Activities—This is Ant," downloaded at http://www.thisisant.com/consumer/ant-in-action/view-activities/ (downloaded on Aug. 3, 2015).

* cited by examiner

*Primary Examiner* — Glenn Richman
(74) *Attorney, Agent, or Firm* — Weitzman Law Offices, LLC

(57) ABSTRACT

An exercise data collection system for use with an exercise machine, including a computerized processing unit and at least two sensors mounted on or near the exercise machine to capture data indicative of aspects of exercising performed by a user of the exercise machine. A first of the at least two sensors being of a first sensor type and a second of the at least two sensors being of a second sensor type different from the first sensor type. The sensors including circuitry associated therewith sufficient to allow the sensors to wirelessly communicate captured data for receipt and analysis by the processing unit, which includes programming that will cause the processing unit to analyze the received captured data in conjunction with characteristics of the user so that a representation of the exercise performed by the user can be constructed that reflects the exercising as it was performed by the user.

20 Claims, 10 Drawing Sheets

EXERCISE DATA COLLECTION SYSTEM

FIELD

This disclosure relates generally to computerized equipment and, more particularly, to computerized exercise equipment.

BACKGROUND

Regular exercise is well known for promoting and maintaining good health. Such exercise has been found by many to be effectively done on exercise machines. Such machines typically have a stationary base and one or more moving parts. At least one of the moving parts is usually moved by the person doing the exercise and the machine often provides resistance to the movement of the part. Moving the part against the resistance is often the essence of the exercise performed on the machine.

Many others prefer to exercise without the use of exercise machines, such as by running or walking on a stationary surface, doing calisthenics, or jumping rope. Still others prefer to employ exercise routines that include exercises performed using machines and other exercises in which machines are not employed. An exercise routine including different exercises is sometimes referred to as "cross training." Further, some prefer to do only one form of exercise but change the form of exercise from time to time. For example, an individual may use exercise machines for a period of time, then cease such use and exercise without using machines, such as by running Employing different forms of exercise, either within a current exercise routine, or serially over different time periods has been found to improve the health and athletic performance of some people.

To accommodate the wide variety of exercises in which people may individually engage, health clubs and other exercise facilities have become very popular because they typically provide different types of exercise machines and spaces where people may perform exercises in which exercise machines are not used. Having a single location in which exercise machines and spaces for other types of exercise are situated has been found to be very convenient and efficient by many people. Consequently, health clubs and other exercise facilities are widely used as the place where many people exercise.

People, who exercise, especially those who exercise regularly, are naturally interested in completing their exercise routines correctly. They are also frequently interested in the physical effects on their bodies and health of the particular exercises they perform. An effective way of ensuring an exercise routine is completed and ascertaining the physical effects thereof is to record specific data related to the exercises immediately after the performance thereof. One way some people accomplish this is by carrying a notebook, journal or diary with them when they exercise and writing data regarding their exercises immediately after they complete the exercise. Such data may include, for example, for a weight-lifting type exercise using an exercise machine, the type of exercise performed, the exercise machine, the number of repetitions of the exercise, the number of sets of repetitions performed (if more than one set), and the magnitude of the weight lifted or resistance provided by the exercise machine.

Handwriting data related to exercise in a notebook or the like can be time-consuming, a distraction from the performance of the exercises, and possibly inaccurate due to the attention that must be given to the various activities associated with exercises. Such activities include not only the physical performance of exercises themselves, but also may include the setting up and adjustment of machines, devices and free weights. Also, the person doing the exercises may be rushed due to personal reasons, for example, exercising during the lunch hour of the person's employment, which may contribute to inaccuracies in the person's handwritten record of data related to the person's exercises.

Useful data related to exercises may be difficult or cumbersome to record by hand. Examples of such data include the amount of time taken to perform specific exercises and time between exercises, the latter of which may provide rest. Such rest periods typically make easier subsequent exercises. Other exercise related data that may be difficult or cumbersome to record by hand is data related to strenuous cardiovascular exercises, such as high speed or distance running, because the person doing such exercise is typically very fatigued immediately after such exercise.

Additional data that is typically difficult or cumbersome to record by hand relates to weight lifting, and the data may include the distance between the weight lifted and the center of mass of the person lifting the weight. This distance is significant because the force that must be exerted by the person to lift the weight generally increases if the distance between the weight and the person's center of mass increases. The making of such a measurement by the person performing an exercise involving weight lifting or locating another to assist in the making of such a measurement would be difficult. This difficulty would be compounded if multiple weight lifting exercises involving different positions and distances relative to the weights were included in a single person's exercise session. The difficulty of recording exercise data by hand may be expected to increase in the future because the types of data available are becoming more numerous due to the increasing complexity and variety of exercises, exercise machines, and other exercise equipment.

A further difficulty associated with exercise related data recorded by hand is that, frequently, it is desired for another person to review the data for interpretation and professional advice regarding the physical effects of specific exercises on the people performing the exercises. Review of the data for interpretation and professional advice may also be sought regarding whether the performance of the exercises could be improved, different exercises should be performed, and the health of the person who performed the exercises to which the data pertained. Consequently, the exercise related data may be advantageously reviewed by, for example, personal trainers, athletic trainers, physical therapists, physician assistants, nurses and doctors. Communicating such data, if recorded by hand, to such individuals may be difficult and cumbersome, especially if such data is complex and substantial in amount. The complexity and amount of such data provided to such individuals will likely increase if such individuals are to provide their optimal professional opinions and advice regarding the physical effects of specific exercises on the people performing the exercises due to the increasingly complexity, detail, scientific nature, and sophistication of exercise, exercise machines and other equipment, medical science, and health care.

Recording exercise related data by hand and communicating such data to others for interpretation and professional advice regarding the data may be difficult and cumbersome.

Thus, there is a technological problem in the art because there is presently no way to accurately capture enough information regarding a person's specific exercise routine such that someone else who is not observing the exercise can, at a later time, have a more complete picture of the person's exercise while it was being performed and its effects over and above the amount of exercise (i.e., repetitions), time expended for that exercise, weight(s) used, and perhaps biometric information such as heart rate.

SUMMARY

In one aspect of this disclosure, an exercise data collection system is disclosed for use with an exercise machine. The exercise data collection system includes a computerized processing unit, and at least two sensors, each mounted on or near the exercise machine, and placed so as to capture data indicative of aspects of exercising performed by a user of the exercise machine. A first of the at least two sensors is a first sensor type and a second of the at least two sensors is a second sensor type different from the first sensor type. The at least two sensors have associated circuitry sufficient to allow the at least two sensors to wirelessly communicate captured data for receipt and analysis by the computerized processing unit. The computerized processing unit includes programming that will cause the computerized processing unit to analyze the received captured data in conjunction with characteristics of the user so that a representation of the exercise performed by the user can be constructed that reflects the exercising as it was performed by the user.

Another aspect involves an exercise data collection system kit for use with an exercise machine. The kit includes at least two sensors, a first of the at least two sensors being of a first sensor type and a second of the at least two sensors being of a second sensor type different from the first sensor type, the at least two sensors incorporating circuitry sufficient to allow the at least two sensors to wirelessly communicate captured data, instructions for mounting the at least two sensors on or near the exercise machine so that the at least two sensors will capture data indicative of aspects of exercising performed by a user of the exercise machine, and a receiver which, in operation, will receive the wirelessly communicated captured data from the at least two sensors and transfer signal-based information reflective of the exercising performed by the user of the exercise machine for analysis.

The foregoing has outlined rather generally the features and technical advantages of one or more embodiments of this disclosure in order that the following detailed description may be better understood. Additional features and advantages of this disclosure will be described hereinafter, which may form the subject of the claims of this application.

BRIEF DESCRIPTION OF THE DRAWINGS

This disclosure is further described in the detailed description that follows, with reference to the drawings, in which.

Corresponding reference characters indicate corresponding parts throughout the several views of the drawings.

DETAILED DESCRIPTION

This application discloses an exercise data collection system 100 and a method of operating the system 700. The data collection system 100 is well suited for use with one or more exercise machines 105 in a health club or other exercise facility, such as a medical evaluation or rehabilitation facility, although the system 100 may also be used in other settings.

Figure 1:
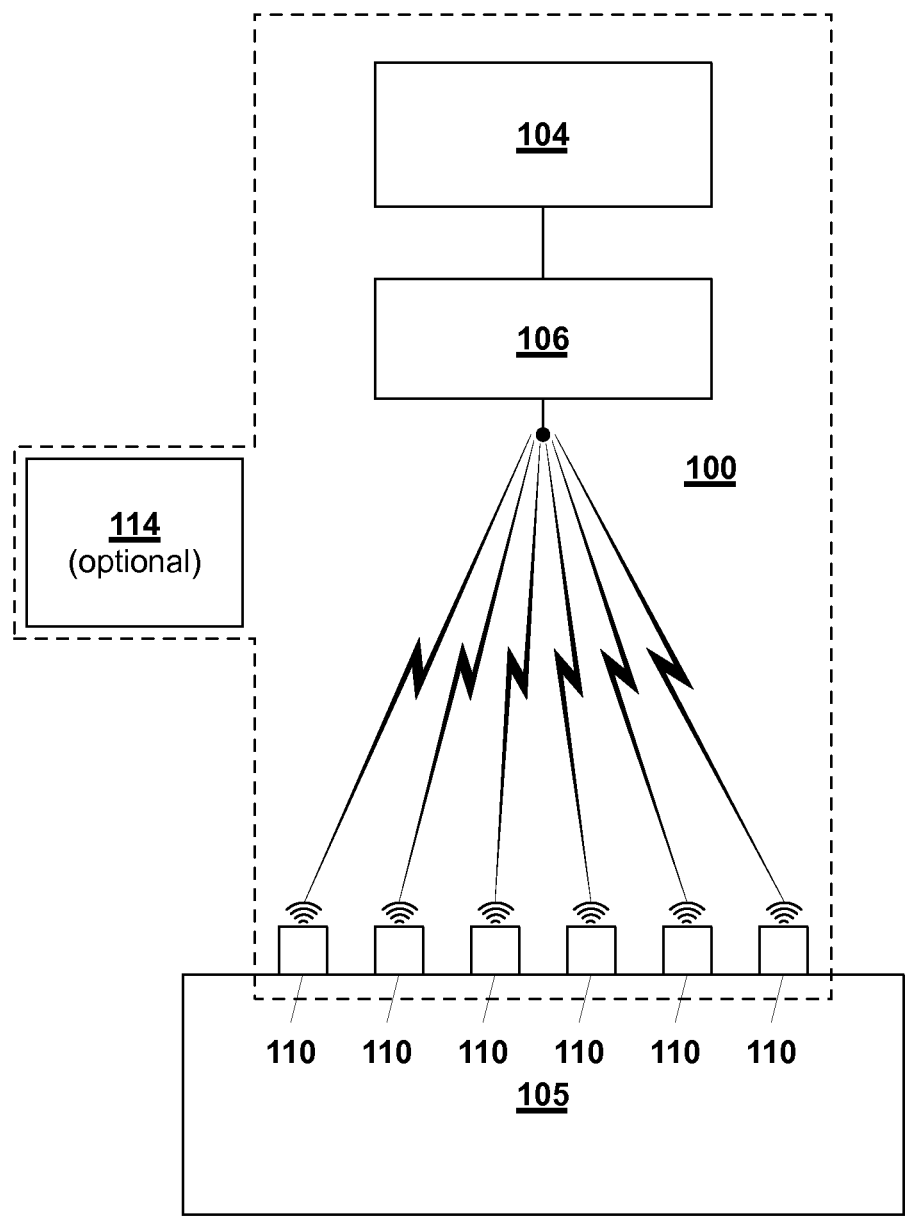
FIG. 1 illustrates, in simplified form, one example implementation of the exercise data collection system deployed on an exercise machine.

FIG. 1 illustrates, in simplified form, one example implementation of the exercise data collection system 100 deployed on an exercise machine 105.

One of the significant advantages of the system 100 is its ability to detect and collect data for an entire workout that includes different types of exercises on different exercise machines. The data collection system 100 processes the collected data to provide analysis and interpretations thereof. The information resulting from the data processing may relate, for example, to the adequacy with which the exercises were performed and the physical effects thereof on the system user 102. This information can be useful to the user 102 of the system 100 and possibly others such as (but not limited to) trainers and/or other health care professionals. Accordingly, some implementations of the system 100 are able to automatically communicate the data and/or any analysis and interpretations thereof in a readily understandable form, such as (but not limited to) one or more tables, graphs or charts to the user 102 and/or others.

The data collection system 100 includes a processing unit 104, including non-transient program and data storage and at least one computer processor, for example, a microprocessor. The data collection system 100 also includes at least one receiver 106, one or more sensors, for example in the case of FIG. 1, six sensors 110, and optionally, a user identification device 114. Each of the sensors 110 is configured so that data indicative of some aspect of the exercise is captured, for example, the force applied by the user 102 during the exercise, the displacement of a piece of the exercise machine 105 representative of motion and its range (and possibly direction) caused by the user 102, the rate of change in velocity of a part of the exercise machine 105 in a direction caused by the exercise of the user 102, to name a few. The captured data (and potentially other information, for example, a unique identifier, a timing indication, or any other appropriate information) is converted to a signal that can be transmitted wirelessly by the sensor(s) 110. Thus, the terms "sensor" and "sensor(s)" are intended to encompass not only the particular detecting device itself, but may also encompass any additional communication and other electrical, optical and/or electronic circuitry that is part of or associated with the sensor 110 and necessary to effect the appropriate wireless transfer of that data for external analysis.

Some examples of the types of sensors 110 that can be used, by themselves or in multiples or combinations, can include (but are not limited to):

a) as a force sensor to detect force (static and/or dynamic) applied by a user 102 to a part of the exercise machine 105: a quartz force sensor, a load cell, for example, a piezoelectric load cell, a fiber optic load cell, a strain gauge load cell, a piezoresistive load cell, an inductive load cell, a reluctance load cell, a magnetostrictive load cell, a micromachined silicon load cell, or any other type of load or force measurement device that will not interfere with the operation of the exercise equipment 105 and can provide a signal indicative of that detection that can be transferred as data to the receiver 106;

b) as a motion sensor to detect motion of the user 102 and/or of part of the exercise machine 105 and/or velocity: a magnetic sensor, a passive infrared sensor, an "electric eye" sensor, a photodiode array, a microwave sensor, an ultrasonic sensor, a small video camera, or any other type of motion sensing device that will not interfere with the operation of the exercise equipment 105 and can provide a signal indicative of that detection that can be transferred as data to the receiver 106;

c) as an acceleration sensor to detect acceleration of a part of the exercise machine 105 caused by the user 102: a piezoresistive accelerometer, a piezoelectric accelerometer, a capacitive accelerometer, a fiber optic accelerometer, an electro-optical accelerometer, a MEMS accelerometer, or any other type of device capable of detecting velocity change rate and that will not interfere with the operation of the exercise equipment 105 and can provide a signal indicative of that detection that can be transferred as data to the receiver 106; and/or d) as a position sensor to detect change in position of the user 102 and/or a part of the exercise machine 105 or its rate of change: a capacitive transducer, a capacitive displacement sensor, an eddy-current sensor, an ultrasonic sensor, a grating sensor, a Hall effect sensor, a magnetic sensor, an inductive non-contact position sensor, a linear variable differential transformer (LVDT), a differential transformer, a linear variable displacement transformer, a linear variable displacement transducer, a multi-axis displacement transducer, a photodiode array, a piezoelectric transducer, a potentiometer, a rotary encoder, a string potentiometer, a small video camera or any other type of position sensing device that will not interfere with the operation of the exercise equipment 105 and can provide a signal indicative of that detection that can be transferred as data to the receiver 106.

Depending upon the particular implementation, a given sensor 110 may be permanently or removably attached to or near an exercise machine 105, or it may be integrated into the exercise machine 105. Advantageously, removable sensors allow the data collection system 100 to be used with or retrofitted to existing exercise equipment of multiple different manufacturers, whereas integrated sensors incorporated into the exercise equipment allow the manufacturer to place sensors in unobtrusive locations and/or optimize placement. For removable sensors, the sensors can be removably affixed to their appropriate locations in any conventional removable manner using appropriate connection element(s), for example, screws, clips, hook and loop fasteners, for example those sold under the Velcro® brand, cable ties, magnets, tape (single or double sided), certain glues, etc. the important point being the ability to affix and remove the sensor when desired and have it obtain the relevant data when attached, not the particular item used to affix it.

Likewise, depending upon the particular implementation, the one or more receivers 106 may be located near the various exercise machines 105 or they may be strategically located in the vicinity thereof, the important aspect being the ability of the receiver(s) 106 to wirelessly receive data-containing signals indicative of some aspect of the exercise from the appropriate sensor(s) 110, not its placement. Thus, it is to be understood that each sensor will incorporate, or have associated with it, a transmitter that is capable of wirelessly transmitting the output of that sensor 110 to a receiver 106. Depending upon the particular implementation, sensor 110 to receiver 106 transmission can be done using any appropriate signal within the electromagnetic spectrum appropriate for the spacing between them, their respective locations, available power, etc., including, for example, in the frequency range/bands of radio or broadcast television (AM, FM, RF, UHF, VHF, etc.), as well as coherent light (i.e., laser), and signals in the IR or UV range, typically using short-distance wireless communication technologies such as (but not limited to) Wi-Fi, Bluetooth, and near field communication (NFC), or any other appropriate short range wireless communications protocol and approach.

The processing unit 104 is coupled to the receiver(s) 106, either in a wired or wireless manner, depending upon the particular implementation variant, in order to provide the data received from the sensor(s) 110 to the processing unit 104 for processing. Again, depending upon how the system 100 is implemented, the processing unit 104 and receiver(s) 106 may be contained within a common housing, they may be located remote from each other within the same location, or they may be located by a significant distance, requiring communication via, for example, a cellular data connection, the internet, a private network, optical links, radio links, or any other means by which data can pass over a significant distance from one electronic device to another. In some example cases, the processing unit 104 can be a user-supplied device, for example, a cell phone, laptop computer, desktop computer, server or other general purpose computing device (a) running special purpose, non-transient application software, or (b) containing special purpose hardware circuitry, so as to cause the processing unit 104 to perform the operations described herein as attributable to the processing unit 104. Alternatively, in other cases, the processing unit 104 can be a special purpose fitness device supplied by the user, the exercise location (e.g., a gym) or some third party (e.g., medical/rehabilitation personnel), and which contains circuitry and/or one or more processors, memory and programming designed to enable it to specifically interact with the receiver(s) 106 to obtain information indicative of or containing data captured or measured by the sensor(s) 110 and analyze that data, ideally in conjunction with appropriate user-specific data that is input or captured, such as (but not limited to) height, weight, gender, age and even potentially certain biometric information that may be useful/necessary to more accurately analyze the user's exercising, for example, height, weight, leg or arm length(s), heart rate, breathing rate, etc., because, for example, height, arm and/or leg length can affect leverage involved in a particular aspect of an exercise and thereby can influence the difficulty or ease of that exercise for that user.

The processing unit 104 and/or the optional user identification device 114 are typically programmed to non-transiently store data related to one or more physical characteristics of the system user 102. Such physical characteristics may include, for example, the height, weight, gender, age, as well as strength and stamina of the system user 102 as indicated by previous instances of exercising, and may even potentially include certain biometric information that may be useful/necessary to more accurately analyze the user's exercising, for example, leg or arm length(s), resting and/or peak heart rate and/or breathing rate, etc. Such user data can improve the accuracy and comprehensiveness of the analysis in determining the effect on the user 102 from use of the exercise machine 105 because the same machine and settings will have a different effect on different users. For example, lifting a specific amount of weight may be very strenuous and have a weakening effect on a user having a small physique and less muscle tone, whereas a user with a large physique or in much better physical shape may be able to lift that same amount of weight more easily and do more, or faster, repetitions with it. Likewise, two different users may perform the same exercise on the same exercise machine 105 with the same settings, resulting in the same data output, but, based upon their strength and physical characteristics, one user may be under-exerting while the other exercising optimally or over exerting. Thus, data such as the number of user repetitions of a specific exercise, the amount of time taken to perform those repetitions and the exercise and, if the exercise involved moving weight, the amount of weight involved becomes even more meaningful if the physical characteristics of the user 102 are available to the processing unit 104 when it analyzes the data from the sensor(s) 110.

Figure 2:
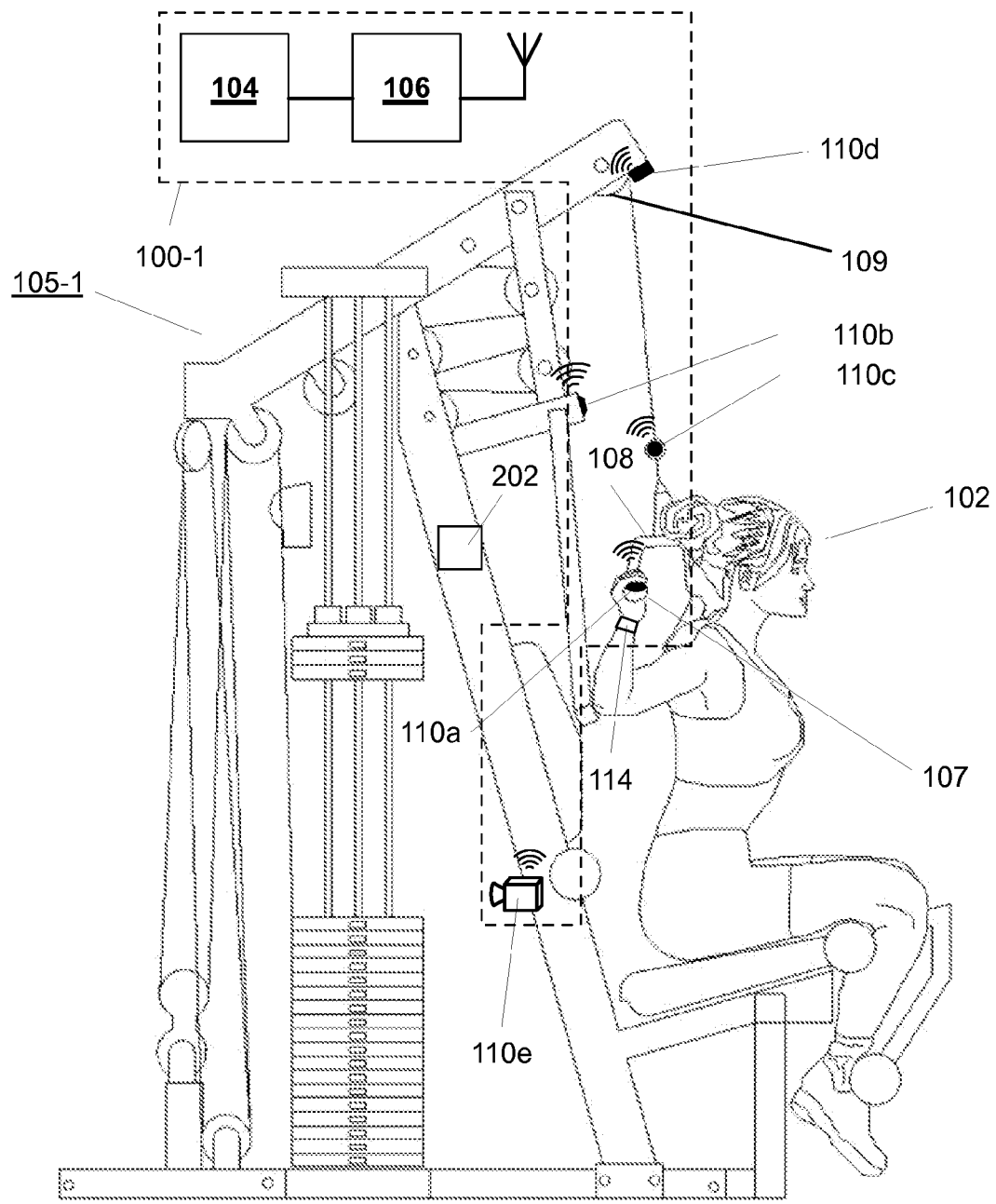
FIG. 2 illustrates, in simplified form, an example implementation of the system used with a representative exercise machine.

FIG. 2 illustrates, in simplified form, an example implementation of the system 100 used with a representative exercise machine 105-1.

As shown in FIG. 2, there are five different, illustrative sensors 110a-110e connected to the particular exercise machine 105, in this case a high pulley station 105-1 type exercise machine 105 that is useful for exercising certain muscles of the back, like the latissimus dorsi and trapezius. As shown in this illustrative example, the sensors include a force sensor 110a, located in the gripping area 107 of the pull-down bar 108, a motion sensor 110b, located on part of the frame structure of the exercise machine 105-1, an accelerometer 110c, located on the cable connected to the pull down bar 108, a position sensor 110d, located on the exercise machine 105 near the upper pulley 109, and a position sensor 110e (which is a small camera or other optical sensor placed so that it can detect the number of plates being moved such that the weight being moved can be determined). All the sensors 110a-110e communicate their respective data to the processing unit 104 of the system 100-1 of FIG. 2 via the receiver 106.

As shown in FIG. 2, the force sensor 110a is a sensor that detects a pulling force exerted on the exercise machine 105-1 by the user 102 while performing the exercise and, in some cases can be used to distinguish among different forces, for example pulling and gripping force. As noted above, the force sensor 110a can be any type of force sensor appropriate for the particular exercise machine 105-1.

The motion sensor 110b is a sensor that is used to detect motion of the relevant portion(s) of the exercise machine 105-1 for purposes of, for example, determining that the machine is being used at all, or, for example, to identify repetitions and/or sets. Likewise, through use of multiple motions sensors 110b, usage aspects such as proper motion through the exercise may be determined.

The acceleration sensor 110c is a sensor that is used to detect changes in motion of some part of the exercise machine 105-1 in one or more directions, for example, to determine how easy it was for a user 102 to move a particular weight, or to determine directional changes of a component of the exercise machine 105-1 indicative of repetitions and/or proper exercise form.

The position sensor 110d is a sensor that is used to detect/measure the position of a part of the exercise machine 105-1, either as an absolute or relative measurement on a linear, angular and/or multi-axis basis, for example, to determine the range of motion through which the user 102 is performing the exercise.

At this point, it should be noted that, in some cases, the same type of sensor 110 can be used to sense different things depending upon its placement and, in still additional cases, the same type of sensor 110 may be able to concurrently act as two different types of sensors.

In addition, it should be noted that the use of sensors, per se, to detect and capture different types of dynamic properties (e.g., force, motion, displacement, velocity, acceleration, etc.) represent the detected dynamic properties as analyzable data, and transfer that data as appropriate electronic signals, is well known and, as such, the details of how to use the sensors and which sensors to use for particular detection are not detailed herein.

Thus, with respect to FIG. 2, through use of the foregoing sensors, data that provides a complete picture of the user's exercise on the exercise machine 105-1 can be captured using the sensors 110 and analyzed by the processing unit 104.

The level of detail for any given sensor may range from whether or not the machine 105 is being used in any manner to the collection of specific data related to the exercise being performed by the system user 102. As such, in aggregate, such specific data could include, for example, for the high pulley exercise machine 105-1 of FIG. 2, data indicative of the amount of weight used, the number of repetitions, how fast and smoothly the user 102 performs each repetition, the distance over which the user 102 moves the part of the machine to which the user is physically applying a force when performing the exercise, and the position of the relevant part(s) of the user 102 throughout each repetition.

Depending upon the particular implementation, the data from each of the sensors 110a-110d may be transmitted to the receiver 106 as the exercise is being performed, it may be transmitted on a periodic basis, or may be buffered along with timing information and transferred thereafter asynchronously as appropriate, the important aspect being that the data is captured and transferred such that the data can be analyzed in conjunction with its timing such that, at any given point in the exercise, a picture of what happened at a particular time can be determined by the processing unit 104 from the data directly, or through interpolation (in the case where data capture is not sufficiently continuous) by reconstructing a continuous function from the data using well-known interpolation algorithms, for example, the Whittaker-Shannon interpolation formula or other interpolation formulas used in digital signal processing.

Figure 3:
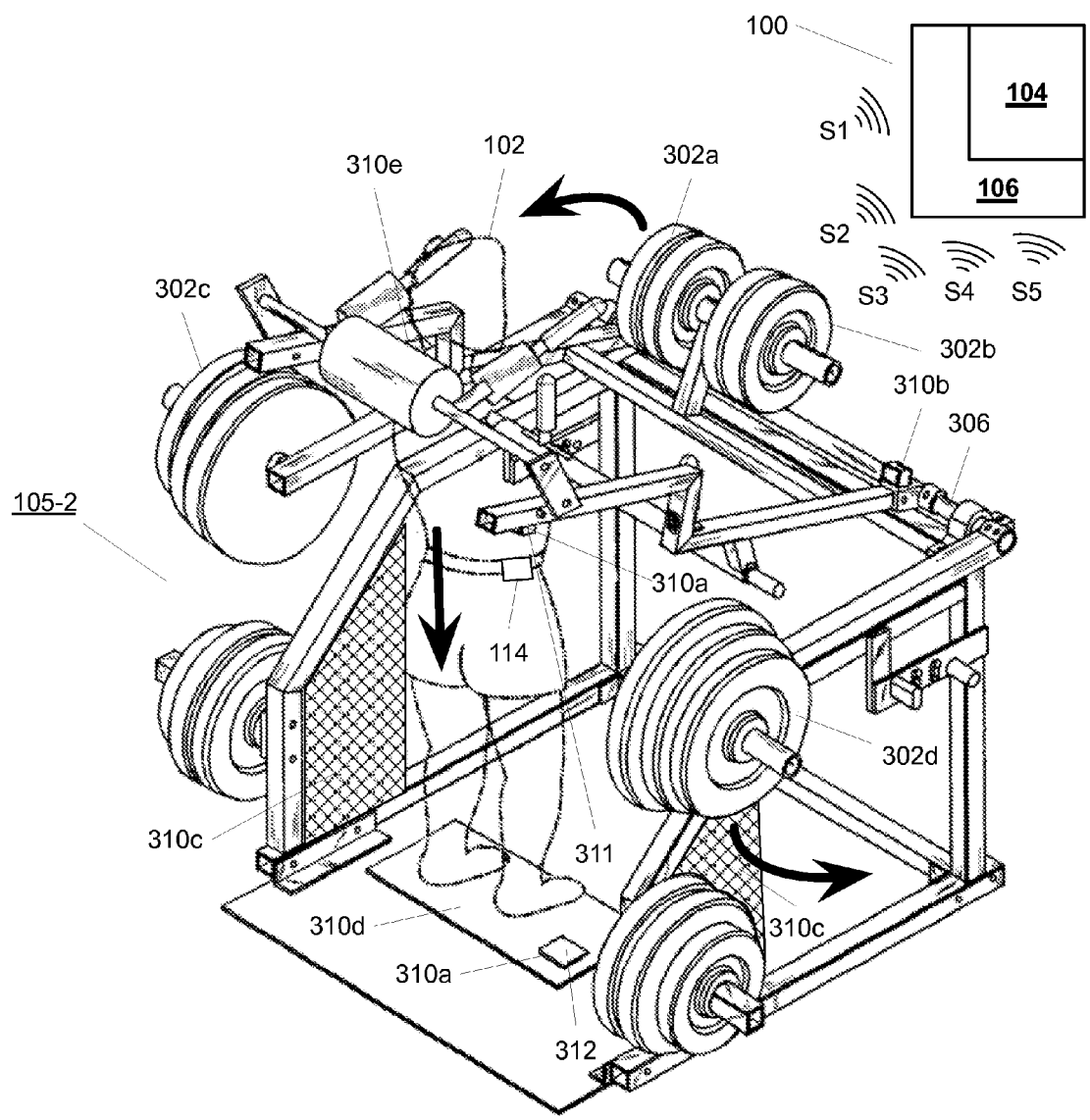
FIG. 3 illustrates, in simplified form, another example deployment of the system for use in connection with another example exercise machine.

FIG. 3 illustrates, in simplified form, another example deployment of the system 100 for use in connection with another example exercise machine 105, in this example, a squat machine 105-2. With this type of exercise machine, the user 102 supports a load, established by the weights 302a-302d, and squats down while supporting the load and then stands back up, thereby lifting the load.

As shown in FIG. 3, five illustrative sensors 310a-310e, such as the sensor(s) 110 described above, are used. One sensor 310a (made up of two parts 311, 312) is a position/movement sensor that detects motion and distance of one of the arms 304 of the exercise machine 105-2 relative to the ground as the exercise is performed. Another sensor 310b detects the amount of angular rotation of the bar 306 that serves as the pivot point. A further sensor 310c is an optical array that captures the posture and depth of the lower portion of the user 102 while the user 102 does the squat exercises. An additional sensor 310d is a load sensor that measures the force exerted by the user 102 during the squat exercises using the user's weight as a tare or unladen weight (force) and using the weight detected as the user supports the load while fully upright as the gross weight (force) so that the actual load being moved by the user can be determined as well as the force exerted during exercise. Another sensor 310e is an accelerometer located under the cushion that rests on the user's 102 shoulders and measures the up/down acceleration of the user's shoulders during the exercise.

As in FIGS. 1 and 2, a version of the system 100, in this case a unitary structure containing the receiver 106 and processing unit 104, is located nearby to wirelessly receive the signals S1-S5 provided by the sensors 310a-310e while the user 102 is exercising, and provide them to the processing unit 104.

Figure 4:
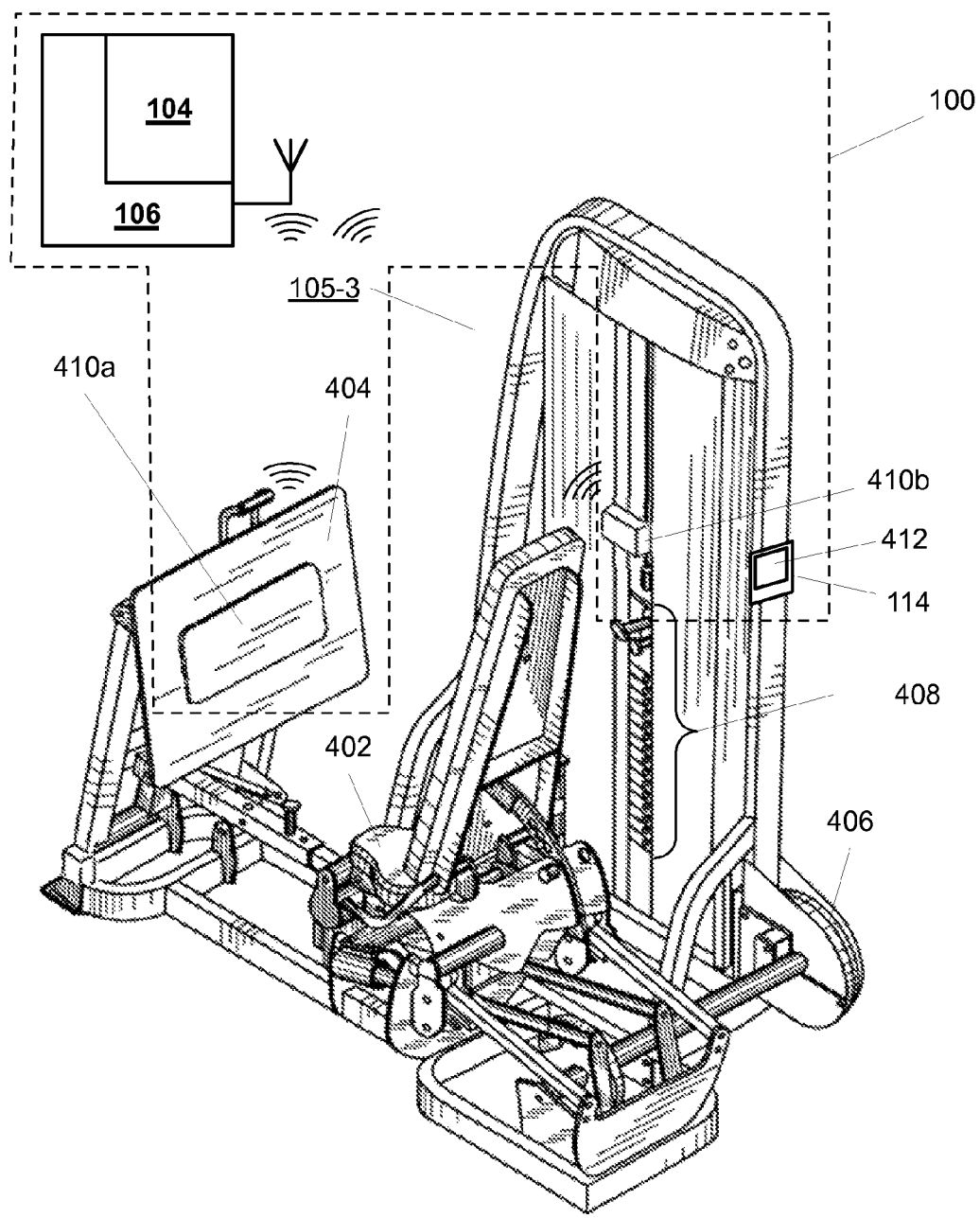
FIG. 4 illustrates, in simplified form, another example deployment of the system for use in connection with another example exercise machine.

FIG. 4 illustrates, in simplified form, another example deployment of the system 100 for use in connection with another example exercise machine 105, in this example, a leg press exercise machine 105-3. With this type of machine, a user (not shown) sits on a seat 402 with the user's feet, when in the resting position, being on the pressure plate 404 typically with the user's legs bent so that the user's knees are near the user's chest. During exercise, the user exerts a force on the plate 404 causing the seat 402 to move away from the plate 404 and, via linkages, cause a pulley 406 to rotate and lift one or more of the set weights 408.

As shown in FIG. 4, two sensors 410a, 410b, of the type of sensors 110 described above, are illustrated. One of the sensors 410a is a load sensor, in this case a load cell, that detects the amount of force exerted by the user on the plate 404 while moving the seat against the force of the weights. The other sensor 410b is a combined position sensor and accelerometer that measures the distance over which the specified weight 408 is moved and its acceleration.

Figure 5:
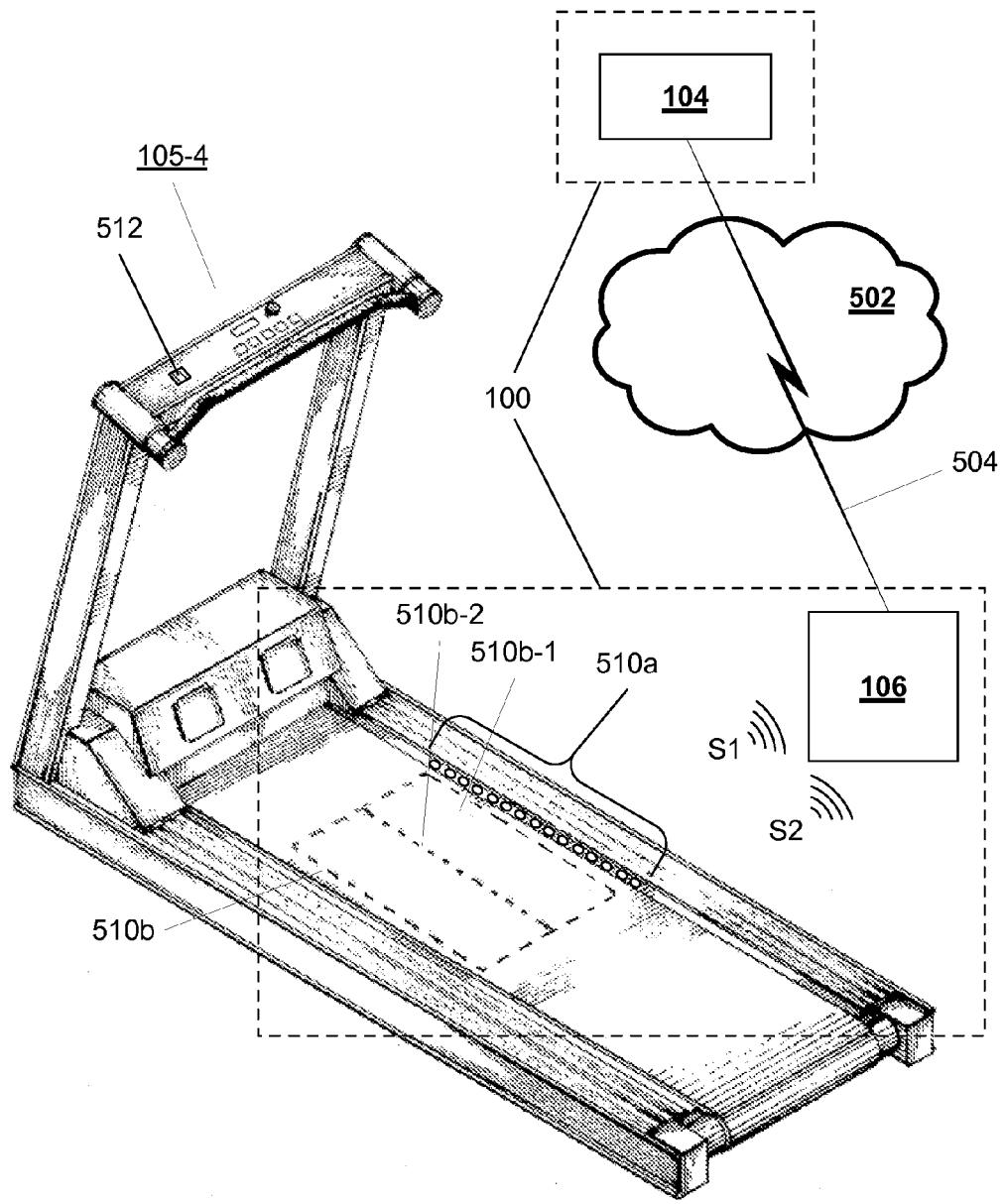
FIG. 5 illustrates, in simplified form, another example deployment of the system for use in connection with another example exercise machine.

FIG. 5 illustrates, in simplified form, another example deployment of the system 100 for use in connection with another example exercise machine 105, in this example, a treadmill 105-4.

As shown in FIG. 5, the treadmill includes two sensors 510a, 510b of the type of sensors 110 described above. One of the sensors 510a is a motion sensor made up of an electric eye array along the internal rail of the treadmill 105-4 that detects the location of the user's feet along the tread. The other sensor 510b is a force sensor located under the tread that includes two parts 510b-1, 510b-2 and is used to discriminate between the user's two feet. In this way, the speed at which the user is walking/trotting/running and the force of each foot landing can be determined.

In this example, the sensors 510a, 510b send their data via wireless signals S1, S2 to a local receiver 106 for forwarding to a remotely located processing unit 104 through a data network 502 via a communication link 504, which may be, for example, a cellular network, the internet, a proprietary network, etc.

Figure 6:
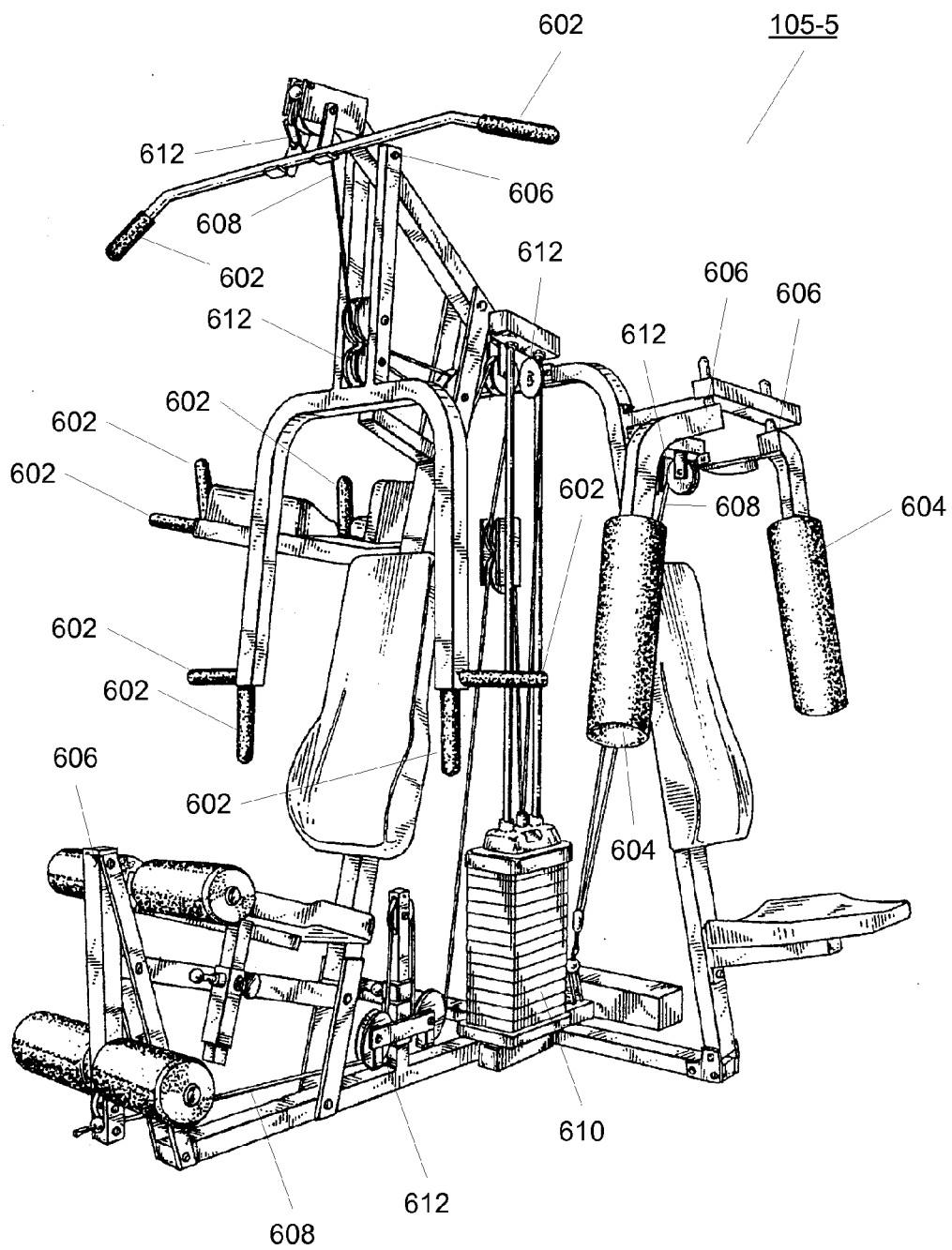
FIG. 6 illustrates, in simplified form, another example of an exercise machine, specifically a multi-station, compound exercise machine, suitable for retrofitting and use with the system and approach described herein.

Advantageously, through the approach described herein, sensor(s) 110 can be placed in or on whatever part of the particular exercise machine 105 is appropriate to obtain an accurate representation of a user's exercise. This is indicated in FIG. 6 which illustrates, in simplified form, another example of an exercise machine 105, specifically, a multi-station, compound exercise machine 105-5, suitable for retrofitting and use with the system 100 and approach described herein.

Some examples of locations suitable for sensor placement on exercise machines 105 in general, and in this specific example case, the exercise machine 105-5, include the outer surfaces of any grips 602 that a system user 102 (not shown) grasps when performing arm exercises on many types of exercise machines. Such grips are often connected to one or more of a pivoted structural member, a displaceable cable or extensible/collapsible/moveable rod, which by applying a force to the grip(s) 602 may be moved by a system user 102 such that the movement is forcibly resisted, at a specified level, by the exercise machine 105 typically by connection to one or more weights, springs or other tension devices.

Another example of suitable sensor placement locations include the outer surfaces of the flat plates (FIG. 4, 404) or bars (FIG. 6, 604), often padded, against which the system user 102 presses part of their arms, feet or legs when performing certain arm, back or leg exercises on many types of exercise machines. Such components 404, 604 are likewise often connected to a pivoted structural member 606 and/or cable 608 that may be moved by the system user against resistance exerted by some portion of the exercise machine 105-5, for example, through weights 610 or springs.

In general, when retrofitting an existing exercise machine or incorporating one or more sensors into a machine during manufacture, a force sensor 110 should ideally be placed on the surface of the exercise machine 105 against which the system user 102 directly applies force so that the sensor 110 will receive the full force exerted by the user 102. This results in a more accurate representation of the user's exerted force due to the absence of mechanical linkages such as pulleys 612, gears and/or rods between the user 102 and a sensor 110. Such mechanical linkages can introduce friction as well as mechanical advantages/disadvantages that can lead to discrepancies between the force detected by the sensor 110 and the force exerted by the system user 102 when performing the exercise on the exercise machine 105. However, advantageously, other sensors 110, such as (but not limited to) motion sensors, position sensors and acceleration sensors, can be placed on or near such components for determining those movements, particularly where they do not require contact to operate.

The sensed parameters are indicative of the level at which the system user 102 is exercising and indicates the intensity of the user's exercise. Specifically, the intensity may be indicated by parameters such as (but not limited to) the magnitude of the force exerted by the system user 102 against the exercise machine 105, velocity or acceleration of a moving part of the exercise machine 105 caused by the system user 102, the time duration of such movements, reversals in direction, and the frequency of and between the movements so as to detect pauses and bursts.

Optional Components

In some implementations, the data collection system 100 may also optionally include a user identification device 114, for example, a tag, a smartphone, a smart watch, or a purpose-built component supplied by the exercise equipment manufacturer, the sensor system manufacturer or the location (e.g., gym). The user identification device 114 identifies the user to the system 100 so that sensed data for that user can be appropriately maintained separate from that of any other user using a different station of the same exercise equipment 105 or a nearby piece of exercise equipment 105.

The user identification device 114 can, in some implementations, optionally also act as a repeater to relay signals from the sensor to the receiver 106 or act as the receiver 106 itself. Depending upon the particular implementation, the user identification device 114 can interoperate with the sensors 110 so that the sensors 110 only detect movement while that user is using the exercise equipment. In other cases, the user identification device 114 operates such that the user 102 must provide some form of input, for example, pressing a button, or as shown in FIG. 4, touching a particular area of a display 412

(as on a tablet or smartphone), scanning a marking (FIG. 5, 512), for example, a bar code or QR code, on the exercise machine 105, or touching the user identification device 114 to a counterpart component (FIG. 2, 202) located on or near the exercise machine 105, before the sensors 110 will be enabled to capture exercise-related data.

As originally shown in FIG. 2, the user identification device 114 is connected to some part of the body of the system user 102, in this case, the user's wrist, using any appropriate method or device including, for example, one or more clips, pins, hook and loop fasteners, straps, etc. As also shown in FIG. 3, user identification device 114 may be attached to the user, for example, by a belt 116 around the system user's waist or to some other part of the user or an article of the user's clothing. Alternatively, the user identification device 114 can simply be a hand-held article the user can carry to the exercise machine 105, or it can be implemented using a keyboard and/or display/touchscreen (FIG. 4, 412) on the exercise machine 105 itself such that the user 102 must enter their identifying information to enable the sensor(s) 110.

Depending upon the particular implementation, the system 100 may also be capable of automatically detecting the physical location and presence of the system user 102, using, for example, one or more global positioning type sensor(s) (GPS), to detect the user identification device 114. Such a GPS sensor configuration may be implemented similar to the GPS devices already found in many types of smart phones and other portable handheld devices. Advantageously, this configuration can eliminate the need for users to identify themselves at every exercise machine 105 because the GPS will allow for automatic identification that the user is at the machine. However, one drawback to this automatic approach is that sometimes users may exercise in groups of two or more people either so that the non-exercising people can provide encouragement or there may be two people present merely because one is conversing with or watching the one exercising. In such a case, a more specific GPS location identification may be necessary, a priority scheme must be used to establish who is exercising, for example, if a first user is detected and exercise sensing is in progress, the identification of a new person being present will be ignored until the exercising stops for a designated period. Alternatively, a secondary sensor can be used to determine which of the persons is actually in the proper place for using the exercise machine 105 and that secondary sensor can override or augment the GPS detection.

If worn by a user 102, other implementations of the user identification device 114 may include a pedometer to detect the system user's 102 steps, for example, during exercise on a stair climbing exercise machine, elliptical trainer or a treadmill. The pedometer can likewise be configured as a sensor 110 so that it generates an electrical signal indicative of the foot steps taken by the system user 102 and can provide that signal to the processing unit 104, directly or via the receiver 106 as appropriate for the particular implementation.

An alternative implementation of the user identification device 114 can simply be a card provided to the system user 102 or an ID tag secured to the body of the system user 102 that is encoded or otherwise contains user-unique identification information. This approach would be usable to the extent the exercise data collection system 100 includes a corresponding device to read the card or tag, for example, optically, acoustically, electronically or electromagnetically, as appropriate for the particular implementation so that users can identify themselves to the system 100.

Operation

Having described the various components of the system 100 and their individual placement and purposes, the operation of the system 100 will now be discussed in connection with FIG. 7, which illustrates, in simplified form, an overview of the process performed by various implementations of the systems described herein.

Figure 7:
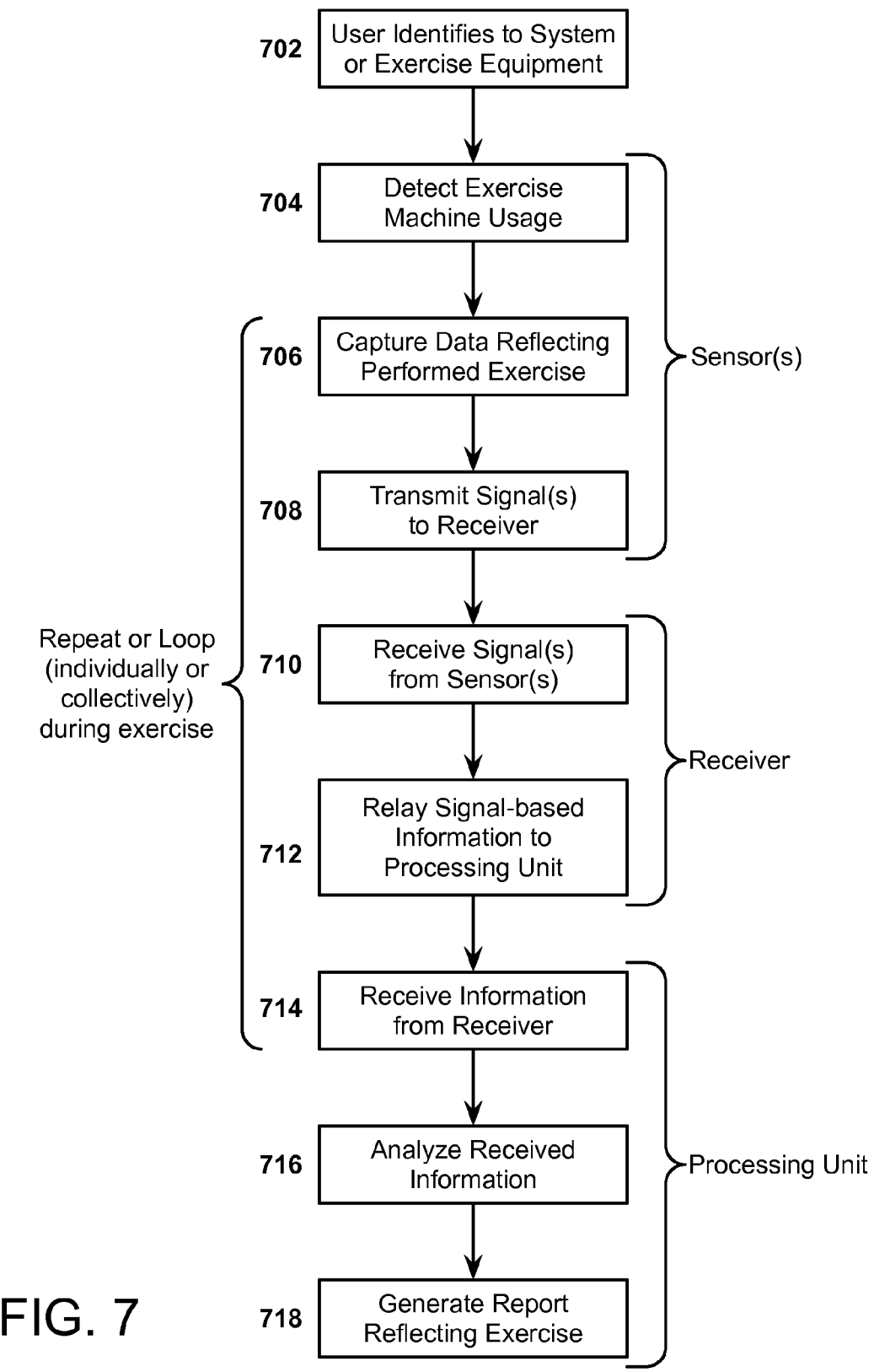
FIG. 7 illustrates, in simplified form, an overview of the process performed by various implementations of the systems described herein.

As shown in FIG. 7, the process begins with the user being identified to the system and/or a particular piece of exercise equipment (Step 702). Once this is complete, the sensor(s) are enabled to detect usage of the exercise machine (Step 704) and begin capturing data reflective of the exercising associated with that usage (Step 706). As noted above, either as the exercise progresses or periodically, the sensor(s) transmit the captured data (potentially along with timing-related information) as signals to the receiver 106 (Step 708). The receiver 106 receives the signals from the sensor(s) 110 (Step 710) and, after performing any appropriate operation with them, relays them to the processing unit 104 (Step 712) as signal-based information. Depending upon the particular implementation, in the simplest case, the receiver 106 will receive those signals and merely relay those signals to the processing unit in an as-received form. In other cases, the receiver 106 may be configured to manipulate the signals in some way that may entail extracting the captured data (and timing information, if present) and combining and/or reformatting it in some way before relaying it to the processing unit 104 or converting it into a different form appropriate for forwarding (for example, by translating from one transmission protocol to another). In still other cases, the receiver 106 can perform some more complex preliminary manipulation of the data, for example, by using the timing information to align data from two or more sensors in the circumstance where sensors do not all concurrently send data as the exercising proceeds or some do and others send data periodically. In any event, the receiver 106 relays the signal-based information to the processing unit 104.

The processing unit 104 then receives the signal-based information from the receiver 106 (Step 714) and analyzes the received information (Step 716) in order to generate a report reflecting the user's exercise (Step 718).

At this point, it is important to note that, in operation and depending upon the implementation, any of individual Steps 706 through 714 may be repeatedly operating in a looping manner. Likewise, certain steps may be occurring concurrently with other steps or in a partially overlapping manner. Thus, it should not be presumed that each of Steps 706 through 716 must complete before the next sequential step begins. Moreover, the steps performed by particular devices (e.g., the sensor(s) 110, receiver 106 and processing unit 104) can be performed sequentially, with a partial overlap, or, in some cases, concurrently or "out of order" to the extent a device further along in the process is operating on earlier data while another device is operating on or awaiting newer data.

Figure 8:
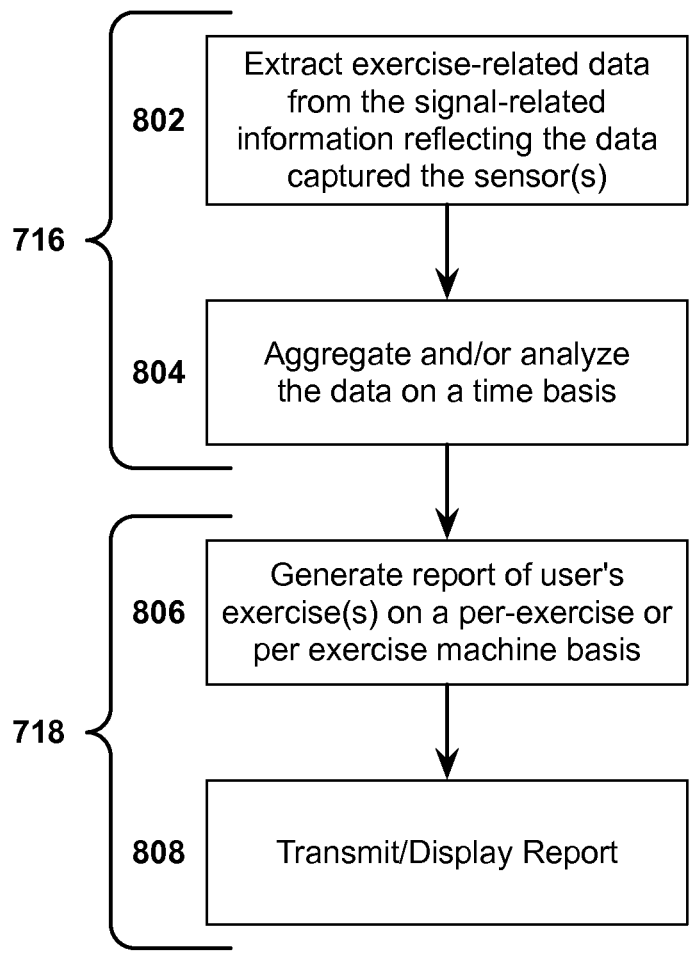
FIG. 8 illustrates, in simplified form, further operational sub-details of the steps preformed by the processing unit.

FIG. 8 illustrates, in simplified form, further operational sub-details of the steps preformed by the processing unit 104. Specifically, as shown in FIG. 8, Step 716 of FIG. 7 includes two sub-steps: (1) extracting the exercise-related data from the signal-related information provided by the receiver 106 (Step 802), and aggregating and analyzing the data on a time basis to get a picture of the user's exercising as reflected in the data (along with any user-specific characteristics, parameters and/or information) (Step 804).

Likewise, Step 718 of FIG. 7 includes two sub-steps (although, in actuality, the two sub-steps may appear to be a single step for some implementations). The first sub-step involves generating a report of the user's exercise(s) on a per-exercise or per-exercise machine basis (Step 806). The second sub-step involves transmitting or displaying the report to the relevant person(s), who may include, for example, one or more of the user, a trainer, a medical person (e.g., doctor, nurse, rehabilitation therapist, etc.) (Step 808).

In Step 802, the meaningful relayed information is extracted using conventional techniques for removing information such that the processing unit 104 retains the association between what was measured/captured, when it was measured/captured, and the data resulting from that measurement/capture.

Next, in Step 804, that information is, as appropriate, aggregated or analyzed so as to achieve an analysis result for the particular exercise that can be represented (Step 806) in a simplified human-understandable form, for example graphically as a chart, with colors, varying thickness lines, or any other meaningful manner, from the sensed data. For example, force, displacement, acceleration and time information, along with the user's heart rate may be combined so that it can be represented graphically for a given weight lifting exercise.

Figure 9:
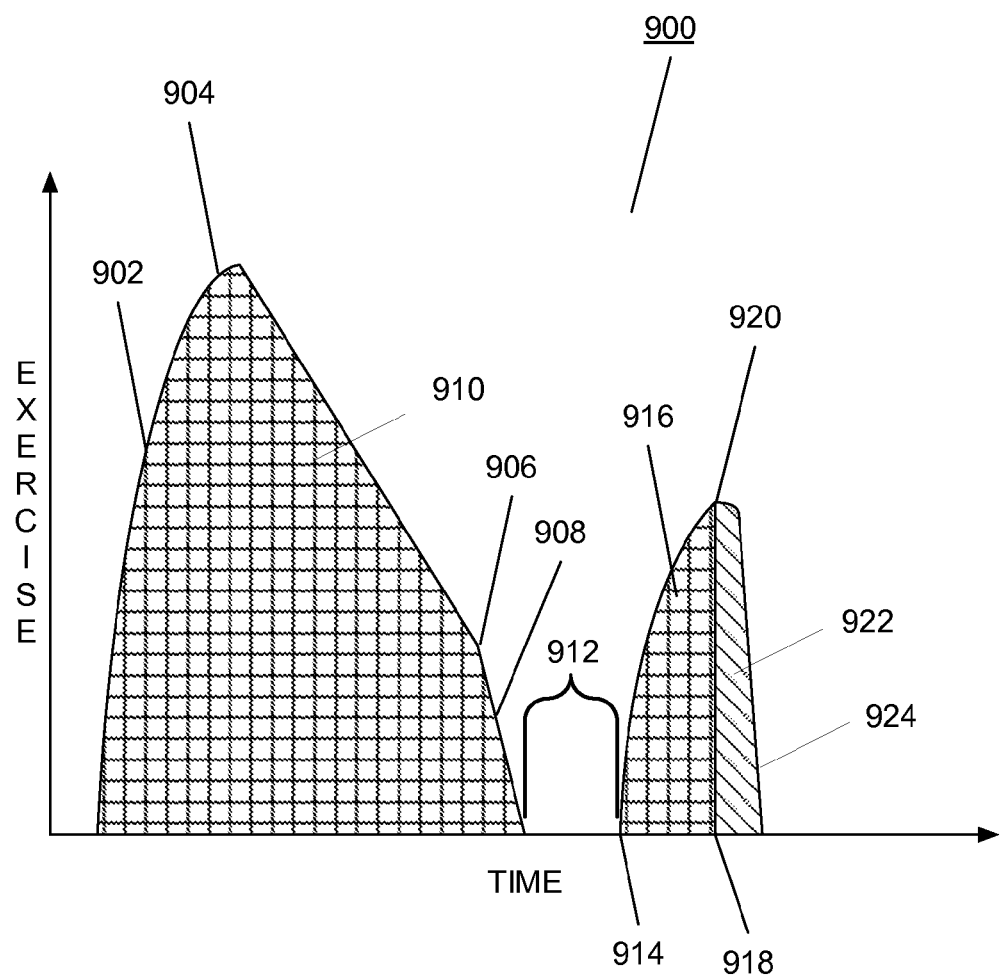
FIG. 9 illustrates, in simplified form, an illustrative graphical representation of a portion of the analyzed data for a weight lifting exercise performed by a user on a particular exercise machine.

By way of specific example, FIG. 9 illustrates, in simplified form, an illustrative graphical representation 900 of a portion of the analyzed data for a weight lifting exercise performed by a user on a particular exercise machine. As shown in FIG. 9, the initial portion 902 of the first represented curve indicates that, during the exercise, the user lifted the weight initially with a substantially constant force and then accelerated the weight near the end 904 of the extension, and then lowered it back down at a slow, constant rate, inflecting 906 to a faster but constant rate 908 near the end of this repetition. In addition, as represented by the grid pattern 910 underneath the curve, the user's heart rate throughout the repetition remained within the acceptable range. The user then rested for a short time 912 and then at time 914 began the next repetition 916 only to find it more difficult. This is evident because, partway 918 through the next repetition, there is an inflection 920 at about the time the user's heart rate goes beyond an acceptable level (as indicated by the changed pattern 922 under the second repetition curve) and, as finally indicated 924, the user abruptly brings down the weight.

Returning to FIG. 8, finally, the analysis result for each exercise and/or exercise machine is organized into a report that can be transmitted or displayed as appropriate (Step 808).

Figure 10:
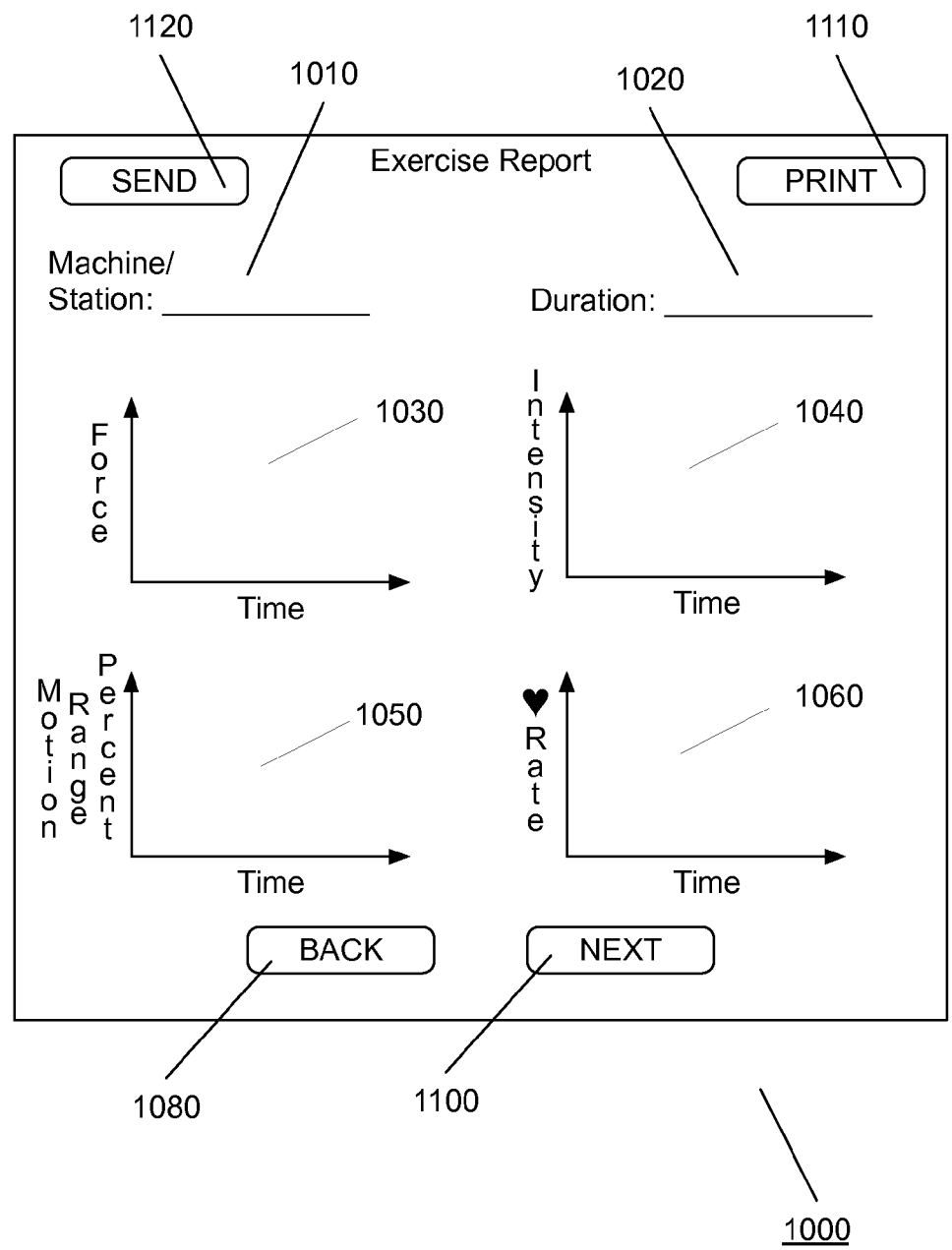
FIG. 10 illustrates, in simplified form, one representative example of a template that is displayable on a computing device and, when populated by the processing unit 104 with the analysis results, would be the report.

FIG. 10 illustrates, in simplified form, one representative example of a template 1000 that is displayable on a computing device, such as a smartphone, touchscreen-containing computer or tablet computer (which may be the processing unit 104 or a different device), such that, when populated by the processing unit 104 with the analysis results, it will be the exercise report. Alternatively, or additionally, a similar specific template suitable for printing on a printer can be provided if necessary.

As shown in FIG. 10, this example template 1000 is for a report of exercise on a machine basis and, thus, includes an area 1010 where the particular exercise machine or machine station can be identified, along with the duration 1020 the exercise on that machine/station lasted. This illustrative template 1000 further includes areas displaying graphs of "force expended versus time" 1030, "exercise intensity versus time" 1040, the percentage of the user's full range of motion used (based upon the user's characteristics) 1050, and the user's heart rate 1060 during the exercise. As further shown, this template includes "Back" 1080 and "Next" 1100 buttons that allow the user to navigate to other screens which may show, for example, appropriate similar information for different exercise machines/stations, user-specific parametric or historical exercise information, or other desired information, on additional screens (not shown).

Finally, this example template also includes a "Print" button 1110 that will allow the user to print out a version of the report (or some portion thereof) on a designated printer, and a "Send" button 1120 that may be used to invoke a transfer program of some sort to allow the user to transfer the report via, for example, e-mail, SMS, MMS, ftp, a "chat"-type program or other file transfer method as implemented for the particular implementation, again, if this aspect is implemented, the important aspect is the ability to transfer a file or files making up the report or the data used to construct it, not the particular transfer method or protocol involved.

At this point, it should be understood and appreciated that there are numerous ways that the analysis results can be displayed or represented and the way that the template or report can be configured, the limit only being the capabilities of the particular devices involved and the need for the result(s) to be understandable. For example, in the future, devices may be capable of allowing the results to be displayed in three dimensions using some form of holographic display. Such a display of a report should likewise be considered to be within the intent of the reports described herein because the important aspect is that the analysis results are presentable in some meaningful fashion to the desired person(s), not the means by which they are displayed.

Other Implementations

Finally, since an advantage of various implementations of the system 100 described herein is the ability to retrofit it to an existing exercise machine 105, a further implementation involves a "kit" form of the system 100 made up of a package containing the sensors 110 for a particular style of exercise machine or station thereof, along with placement and attachment instructions and, for some local implementations of the kit, one or more receivers 106 and a processing unit 104 containing programming specifically designed for the purpose. In this manner, the system can be distributed in a "turnkey" fashion requiring minimal expertise to set up and operate. Other implementations of the kit can omit the processing unit 104 from the kit, for example, if that aspect is centrally provided as a service and network accessible (for example, a cloud-based service). In still other implementations of the kit, a computer program storage medium, for example, a CD, DVD, solid state memory device, etc., containing the program(s) necessary to allow a computer device to act a the processing unit 104 can be provided in the kit or can be made available for download and installation (to a purchaser of the kit or a user of the exercise equipment) to a computer device that will, when running the program(s), act as the processing unit 104.

The foregoing description of various embodiments in this disclosure has been presented for purposes of illustration and description. It is not intended to be exhaustive or to limit the invention to the precise form or embodiments disclosed. Many modifications and variations are possible. Such modifications and variations that may be apparent to a person skilled in the art are intended to be included within the scope of the invention as defined by the appended claims.

What is claimed is:

1. An exercise data collection system for use with an exercise machine including a movable mass, comprising:
    a computerized processing unit; and
    at least two sensors, each mounted on or near the exercise machine, and placed so as to capture data indicative of aspects of exercising performed by a user of the exercise machine while moving the movable mass, a first of the at least two sensors being of a first sensor type and a second of the at least two sensors being of a second sensor type different from the first sensor type, the at least two sensors having circuitry associated therewith sufficient to allow the at least two sensors to wirelessly communicate captured data, including data reflective of a range of motion of the user, for receipt and analysis by the computerized processing unit; and the computerized processing unit including programming that will cause the computerized processing unit to analyze the received captured data in conjunction with physical characteristics of the user, including at least the user's leg or arm length, so that a representation of the exercise performed by the user, including range of motion, can be constructed that reflects the exercising as it was performed by the user.

2. The exercise data collection system of claim 1, further comprising:
a user identification device that allows the user to establish when the at least two sensors should begin capturing data.

3. The exercise data collection system of claim 1, wherein one of the at least two sensors comprises a force sensor that captures information from the exercise machine indicative of a magnitude of force exerted on a part of the exercise machine by the user during the user's exercise involving the exercise machine.

4. The exercise data collection system of claim 3, wherein the force sensor comprises at least one of:
a quartz force sensor, a load cell, a piezoelectric load cell, a fiber optic load cell, a strain gauge load cell, a piezoresistive load cell, an inductive load cell, a reluctance load cell, a magnetostrictive load cell, or a micromachined silicon load cell.

5. The exercise data collection system of claim 1, wherein one of the at least two sensors comprises a motion sensor that detects at least one of motion of the user or a part of the exercise machine.

6. The exercise data collection system of claim 5, wherein the motion sensor comprises at least one of:
a passive infrared sensor, an "electric eye" sensor, a photodiode array, a microwave sensor, an ultrasonic sensor, or a small video camera.

7. The exercise data collection system of claim 1, wherein one of the at least two sensors comprises an acceleration sensor.

8. The exercise data collection system of claim 7, wherein the acceleration sensor comprises at least one of:
a piezoresistive accelerometer, a piezoelectric accelerometer, a capacitive accelerometer, a fiber optic accelerometer, an electro-optical accelerometer, or a MEMS accelerometer.

9. The exercise data collection system of claim 1, wherein one of the at least two sensors comprises a position sensor.

10. The exercise data collection system of claim 9, wherein the position sensor comprises at least one of:
a capacitive transducer, a capacitive displacement sensor, an eddy-current sensor, an ultrasonic sensor, a grating sensor, a Hall effect sensor, an inductive non-contact position sensor, a linear variable differential transformer (LVDT), a differential transformer, a linear variable displacement transformer, a linear variable displacement transducer, a multi-axis displacement transducer, a photodiode array, a piezoelectric transducer, a potentiometer, a rotary encoder, or a string potentiometer.

11. The exercise data collection system of claim 1, wherein one of the at least two sensors comprises a pedometer.

12. The exercise data collection system of claim 1, further comprising a user identification device, recognizable by the system, that allows the sensors to capture data representative of exercise performed using the exercise machine.

13. The exercise data collection system of claim 1, wherein at least one of a user identification device or the computerized processing unit non-transiently stores the characteristics of the user.

14. The exercise data collection system of claim 1, further comprising:
a receiver communicatively interposed between the at least two sensors and the computerized processing unit such that the captured data wirelessly communicated by the sensors will be received by the receiver and relayed to the computerized processing unit.

15. The exercise data collection system of claim 14, wherein the receiver modifies the captured data before relaying it to the computerized processing unit.

16. The exercise data collection system of claim 15, wherein the modifying by the receiver includes combining data received from the at least two sensors on the basis of time information.

17. The exercise data collection system of claim 1, wherein the at least two sensors are removably mounted on the exercise machine.

18. The exercise data collection system of claim 1, wherein one of the at least two sensors wirelessly communicates captured exercise-related data one of: (i) periodically while exercising is being performed by the user of the exercise machine, or (ii) after a portion of the exercising by the user is complete.

19. An exercise data collection system kit for use with an exercise machine including a movable mass, the kit comprising:
at least two sensors, a first of the at least two sensors being of a first sensor type and a second of the at least two sensors being of a second sensor type different from the first sensor type, the at least two sensors incorporating circuitry sufficient to allow the at least two sensors to wirelessly communicate captured data including data reflective of a range of motion of the user;
instructions for mounting the at least two sensors on or near the exercise machine so that the at least two sensors will capture data indicative of aspects of exercising performed by a user of the exercise machine while moving the movable mass; and
a receiver which, in operation, will receive the wirelessly communicated captured data from the at least two sensors and then transfer signal-based information reflective of the exercising, including range of motion, performed by the user of the exercise machine for analysis.

20. The exercise data collection system kit for use with an exercise machine of claim 19, further comprising:
a processing unit; and
a storage medium containing programming for the processing unit that, when executed by the processing unit, will cause the processing unit to analyze the signal-based information received from the receiver in conjunction with physical characteristics of the user, including at least the user's leg or arm length, and generate a report resulting therefrom.

* * * * *